(12) United States Patent
Stabelfeldt et al.

(10) Patent No.: US 10,413,454 B2
(45) Date of Patent: Sep. 17, 2019

(54) GENDER-DIFFERENTIATED ABSORBENT ARTICLES

(71) Applicant: Kimberly-Clark Worldwide, Inc., Neenah, WI (US)

(72) Inventors: Sara Jane Wille Stabelfeldt, Appleton, WI (US); Georgia Lynn Zehner, Larsen, WI (US); Nancy Ellen Dawson, Winnebago, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 250 days.

(21) Appl. No.: 15/303,276

(22) PCT Filed: Aug. 27, 2014

(86) PCT No.: PCT/US2014/052904
§ 371 (c)(1),
(2) Date: Oct. 11, 2016

(87) PCT Pub. No.: WO2016/032456
PCT Pub. Date: Mar. 3, 2016

(65) Prior Publication Data
US 2017/0027768 A1 Feb. 2, 2017

(51) Int. Cl.
*A61F 13/15* (2006.01)
*A61F 13/491* (2006.01)
*A61F 13/537* (2006.01)

(52) U.S. Cl.
CPC ...... *A61F 13/491* (2013.01); *A61F 13/15699* (2013.01); *A61F 13/15707* (2013.01);
(Continued)

(58) Field of Classification Search
CPC .......... A61F 13/491; A61F 2013/53739; A61F 13/4915
See application file for complete search history.

(56) References Cited

U.S. PATENT DOCUMENTS 2,952,260 A * 9/1960 Burgeni ................ A61F 13/536
428/163
3,559,648 A * 2/1971 Mason, Jr. ............ A61F 13/493
604/365
(Continued)

FOREIGN PATENT DOCUMENTS

FR 2589047 A1 4/1987
GB 2237205 A 5/1991
(Continued)

*Primary Examiner* — Bradley H Philips
(74) *Attorney, Agent, or Firm* — Kimberly-Clark Worldwide, Inc.

(57) ABSTRACT

A method for manufacturing an absorbent article having a body facing liner, a backsheet coupled to the body facing liner, an absorbent body positioned between the body facing liner and the backsheet, and a fluid acquisition layer having a body facing surface and a garment facing surface, the fluid acquisition layer being positioned between the body facing liner and the backsheet includes providing a web of body facing liner material in face-to-face relation to a web of fluid acquisition layer material, bonding the body facing liner material to the fluid acquisition layer material using an embossing roller, wherein the embossing roller has an axis and a circumferential surface having a circumferential lane, the circumferential lane having azimuthally-alternating target zone and channel zone embossing patterns, and phasing the embossing roller relative to the web to produce female products and male products.

11 Claims, 6 Drawing Sheets

(52) U.S. Cl.
 CPC .. *A61F 13/15723* (2013.01); *A61F 13/15731* (2013.01); *A61F 13/15739* (2013.01); *A61F 13/537* (2013.01); *A61F 2013/15918* (2013.01)

(56) References Cited

U.S. PATENT DOCUMENTS

| | | | |
|---|---|---|---|
| 3,766,922 A | 10/1973 | Krusko | |
| 3,881,490 A * | 5/1975 | Whitehead | A61F 13/533 604/366 |
| 4,037,602 A * | 7/1977 | Hawthorne | A61F 13/493 604/375 |
| 4,560,381 A * | 12/1985 | Southwell | A61F 13/505 2/406 |
| 4,781,710 A * | 11/1988 | Megison | A61F 13/47 604/378 |
| 4,823,783 A * | 4/1989 | Willhite, Jr. | A61F 13/15699 602/52 |
| 4,854,984 A * | 8/1989 | Ball | A44B 18/0011 156/290 |
| 4,950,264 A * | 8/1990 | Osborn, III | A61F 13/15203 604/385.08 |
| 5,019,070 A * | 5/1991 | Ruben | A61F 13/49004 604/379 |
| 5,021,050 A * | 6/1991 | Iskra | A61F 13/53713 604/368 |
| 5,135,521 A * | 8/1992 | Luceri | A61F 13/512 428/137 |
| 5,234,422 A * | 8/1993 | Sneller | A61F 13/15 604/385.25 |
| 5,451,442 A | 9/1995 | Pieniak et al. | |
| 5,518,801 A * | 5/1996 | Chappell | A61F 13/15707 428/152 |
| 5,597,437 A * | 1/1997 | Lange | A61F 13/15699 156/259 |
| 5,613,960 A * | 3/1997 | Mizutani | A61F 13/53747 604/358 |
| D392,736 S * | 3/1998 | Erickson | D24/124 |
| 5,766,389 A * | 6/1998 | Brandon | A61F 13/15 156/229 |
| 5,830,296 A * | 11/1998 | Emenaker | A61F 13/15 156/219 |
| 6,069,294 A * | 5/2000 | Leclercq | A61F 13/15674 156/100 |
| D439,057 S * | 3/2001 | Bissah | D24/125 |
| 6,488,670 B1 | 12/2002 | Schild et al. | |
| 6,673,418 B1 * | 1/2004 | DeOlivera | A61F 13/474 428/141 |
| 6,921,570 B2 * | 7/2005 | Belau | A44B 18/0011 428/100 |
| 7,145,054 B2 * | 12/2006 | Zander | A61F 13/4756 604/380 |
| 7,686,790 B2 * | 3/2010 | Rasmussen | A61F 13/4756 604/317 |
| 8,079,995 B2 | 12/2011 | Tachauer et al. | |
| 8,211,078 B2 * | 7/2012 | Noel | A61F 13/15203 604/385.101 |
| 8,361,045 B2 * | 1/2013 | Thorson | A61F 13/15804 604/367 |
| 8,847,002 B2 * | 9/2014 | Goh | A61F 13/47263 604/378 |
| 9,000,254 B2 | 4/2015 | McGregor et al. | |
| 9,216,117 B2 | 12/2015 | Hwang et al. | |
| 9,492,328 B2 * | 11/2016 | Jackels | A61F 13/15658 |
| 2002/0004654 A1 * | 1/2002 | Daniels | A61F 13/511 604/380 |
| 2003/0114811 A1 * | 6/2003 | Christon | A61F 13/15203 604/362 |
| 2003/0114818 A1 * | 6/2003 | Benecke | A61F 13/505 604/378 |
| 2003/0119404 A1 | 6/2003 | Belau et al. | |
| 2004/0122413 A1 * | 6/2004 | Roessler | A61F 13/15723 604/386 |
| 2004/0267220 A1 | 12/2004 | Hull et al. | |
| 2005/0064058 A1 * | 3/2005 | Lake | B31F 1/07 425/194 |
| 2005/0085783 A1 * | 4/2005 | Komatsu | A61F 13/4704 604/385.04 |
| 2005/0109442 A1 | 5/2005 | Neubauer et al. | |
| 2005/0113791 A1 | 5/2005 | Neubauer et al. | |
| 2005/0148971 A1 | 7/2005 | Kuroda et al. | |
| 2005/0256477 A1 | 11/2005 | Van Gompel et al. | |
| 2005/0256757 A1 | 11/2005 | Sierra et al. | |
| 2007/0049889 A1 * | 3/2007 | Larson | A61F 13/51496 604/380 |
| 2007/0073261 A1 * | 3/2007 | Ashton | A61F 13/15203 604/389 |
| 2007/0233026 A1 * | 10/2007 | Roe | A61F 13/42 604/361 |
| 2008/0249495 A1 * | 10/2008 | Di Virgilio | A61F 13/15756 604/385.01 |
| 2009/0264851 A1 | 10/2009 | Richlen et al. | |
| 2010/0108554 A1 | 5/2010 | Melius et al. | |
| 2011/0004176 A1 * | 1/2011 | Andersson | A61F 13/512 604/378 |
| 2012/0234475 A1 * | 9/2012 | Paldey | A61F 13/15699 156/220 |
| 2013/0261578 A1 | 10/2013 | Hwang et al. | |
| 2013/0261579 A1 * | 10/2013 | Hwang | A61L 15/58 604/365 |
| 2013/0261582 A1 | 10/2013 | Hwang et al. | |
| 2013/0261583 A1 | 10/2013 | Hwang et al. | |

FOREIGN PATENT DOCUMENTS

| | | |
|---|---|---|
| WO | WO 1999/058092 A1 | 11/1999 |
| WO | WO 2003/041626 A1 | 5/2003 |
| WO | WO 2012/125537 A1 | 9/2012 |

\* cited by examiner

GENDER-DIFFERENTIATED ABSORBENT ARTICLES

BACKGROUND

One of the primary functions of personal care absorbent articles is to retain and absorb body exudates such as urine, fecal material, blood, and menses. Along these lines, a desired attribute of personal care absorbent articles is to minimize the leakage of such exudates from the absorbent article. It is also desired, however, that personal care absorbent articles retain and absorb the body exudates in such a fashion so as to provide a dry feel to the wearer, removing exudates from against the skin at the time of the initial insult of the exudate as well as retaining them away from the skin after such insult.

Improvements in leakage minimization have been achieved through gender specific products, where gender differentiation generally includes product aesthetics (print patterns, colored components, etc.) and absorbent/intake layer modifications that design the product toward boy/girl insult zone differences, such as varying surge layer placement between boy- and girl-intended products. Inefficiencies in manufacturing are introduced in producing what are essentially two different products.

Thus, there remains a need for an absorbent article that can provide increased efficiency of intake of body exudates into the absorbent body and improved handling of body exudates to minimize the amount of body exudates in contact with the wearer's skin, but with features similar enough to be considered the same product.

SUMMARY

In one aspect, the disclosure provides for a method for manufacturing an absorbent article having a body facing liner, a backsheet coupled to the body facing liner, an absorbent body positioned between the body facing liner and the backsheet, and a fluid acquisition layer having a body facing surface and a garment facing surface, the fluid acquisition layer being positioned between the body facing liner and the backsheet. The method includes providing a web of body facing liner material in face-to-face relation to a web of fluid acquisition layer material, bonding the body facing liner material to the fluid acquisition layer material using an embossing roller, wherein the embossing roller has an axis and a circumferential surface having a circumferential lane, the circumferential lane having azimuthally-alternating target zone and channel zone embossing patterns, and phasing the embossing roller relative to the web to produce female products and male products.

In another aspect, the disclosure provides for an absorbent article including a longitudinal axis and a lateral axis being defined in a plane parallel to the absorbent article in a laid flat configuration, the absorbent article having a front waist region and a crotch region. The absorbent article includes a body facing liner, a backsheet coupled to the body facing liner, and an absorbent body positioned between the body facing liner and the backsheet. The absorbent article also includes a fluid acquisition layer having a body facing surface and a garment facing surface, the fluid acquisition layer being positioned between the body facing liner and the backsheet, wherein the fluid acquisition is bonded to the body facing liner in a target zone and in a channel zone, wherein the target zone has a bonding pattern different from a bonding pattern of the channel zone, and wherein the target zone is located primarily in the front waist region for an absorbent article intended for males, and primarily in the crotch region for an absorbent article intended for females.

In still another aspect, the disclosure provides for a method for manufacturing an absorbent article having a body facing liner, a backsheet coupled to the body facing liner, an absorbent body positioned between the body facing liner and the backsheet, and a fluid acquisition layer having a body facing surface and a garment facing surface, the fluid acquisition layer being positioned between the body facing liner and the backsheet. The method includes providing a web of body facing liner material in face-to-face relation to a web of fluid acquisition layer material, and bonding the body facing liner material to the fluid acquisition layer material using an embossing roller, wherein the embossing roller has an axis and a circumferential surface, wherein the circumferential surface is divided into at least first and second circumferential lanes, each circumferential lane having azimuthally-alternating target zone and channel zone embossing patterns, and wherein the second circumferential lane is azimuthally offset from the first circumferential lane. The method also includes separating individual body facing liner/fluid acquisition layer combinations from the bonded web.

BRIEF DESCRIPTION OF DRAWINGS

The foregoing and other features and aspects of the present disclosure and the manner of attaining them will become more apparent, and the disclosure itself will be better understood by reference to the following description, appended claims and accompanying drawings, where:

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

In an aspect, the present disclosure is generally directed towards an absorbent article that can have an acquisition layer with at least one channel. Each example is provided by way of explanation and is not meant as a limitation. For example, features illustrated or described as part of one aspect or figure can be used on another aspect or figure to yield yet another aspect. It is intended that the present disclosure include such modifications and variations.

When introducing elements of the present disclosure or the preferred aspect(s) thereof, the articles "a", "an", "the" and "said" are intended to mean that there are one or more of the elements. The terms "comprising", "including" and "having" are intended to be inclusive and mean that there can be additional elements other than the listed elements. Many modifications and variations of the present disclosure can be made without departing from the spirit and scope thereof. Therefore, the exemplary aspects described above should not be used to limit the scope of the disclosure.

The term "absorbent article" refers herein to an article that can be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers that are then sent to a carding process that separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers can be subject to adhesive processes to bind the fibers together such as by the use of powder adhesives. The carded web can be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films that constitute liquid transfer films, as well as films that do not transfer fluids, such as, but not limited to, barrier films, filled films, breathable films, and oriented films.

The term "gsm" refers herein to grams per square meter.

The term "hydrophilic" refers herein to fibers or the surfaces of fibers that are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The terms "male products," "products intended for use by males," and "absorbent articles intended for use by males" refer generally to products with an insult target zone positioned closer to the front waist region of a product. Likewise, the terms "female products," "products intended for use by females," and "absorbent articles intended for use by females" refer generally to products with an insult target zone positioned closer to the crotch region of a product. The gender differences in products are intended to accommodate the gender differences in anatomy.

The term "meltblown" refers herein to fibers formed by extruding a molten thermoplastic material through a plurality of fine, usually circular, die capillaries as molten threads or filaments into converging high velocity heated gas (e.g., air) streams that attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers that can be continuous or discontinuous, are generally smaller than about 0.6 denier, and can be tacky and self-bonding when deposited onto a collecting surface.

The term "nonwoven" refers herein to materials and webs of material that are formed without the aid of a textile weaving or knitting process. The materials and webs of materials can have a structure of individual fibers, filaments, or threads (collectively referred to as "fibers") that can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials that are compliant and that will readily conform to the general shape and contours of the wearer's body.

The term "spunbond" refers herein to small diameter fibers that are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S.

Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an aspect, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an aspect, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material that softens and that can be shaped when exposed to heat and that substantially returns to a non-softened condition when cooled.

The term "user" refers herein to one who fits an absorbent article, such as, but not limited to, a diaper, training pant, youth pant, incontinent product, or other absorbent article about the wearer of one of these absorbent articles. A user and a wearer can be the same person.

Figure 1:
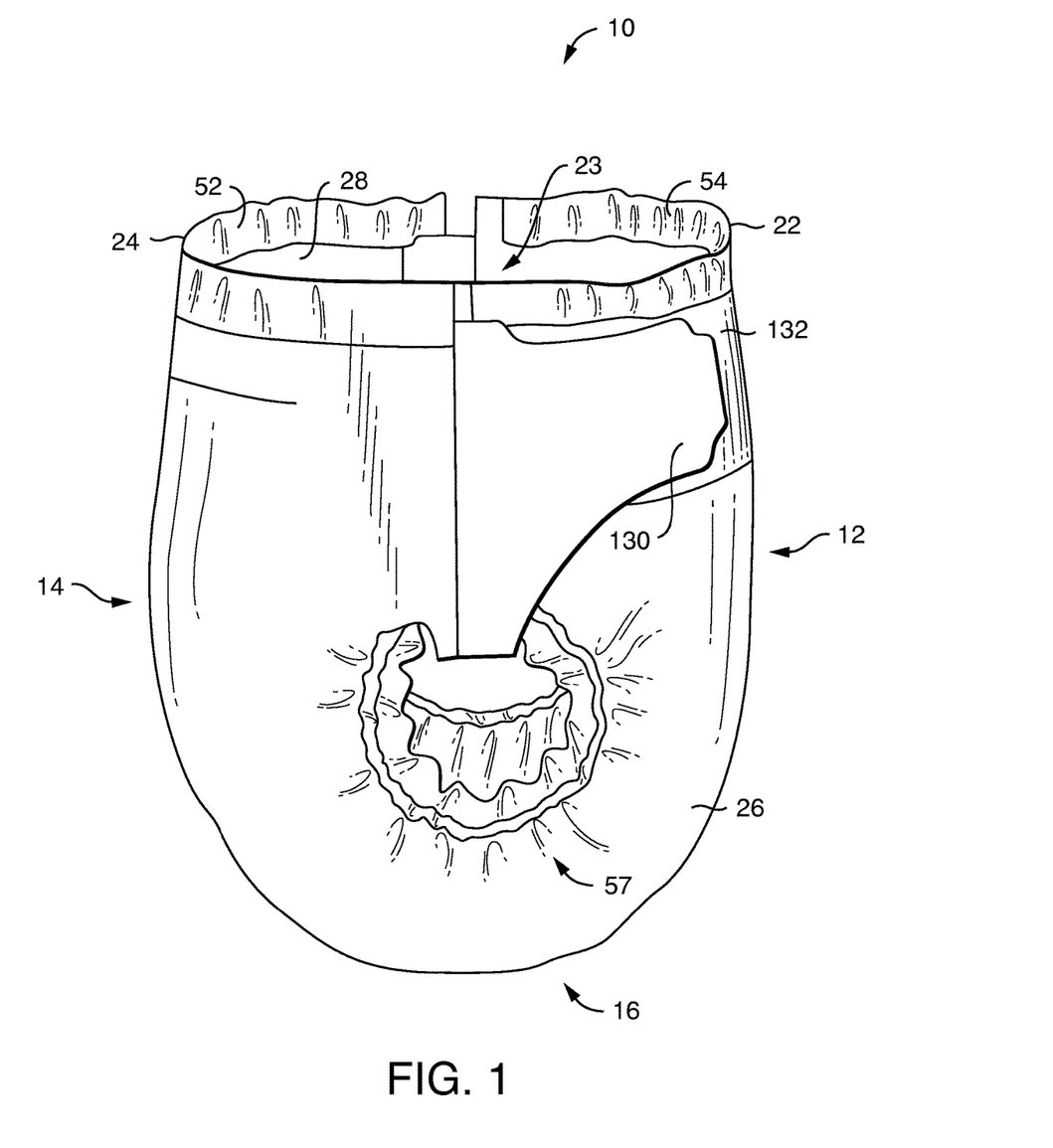
FIG. 1 is a side perspective view of an exemplary aspect of an absorbent article, such as a diaper, in a fastened condition.
Figure 2:
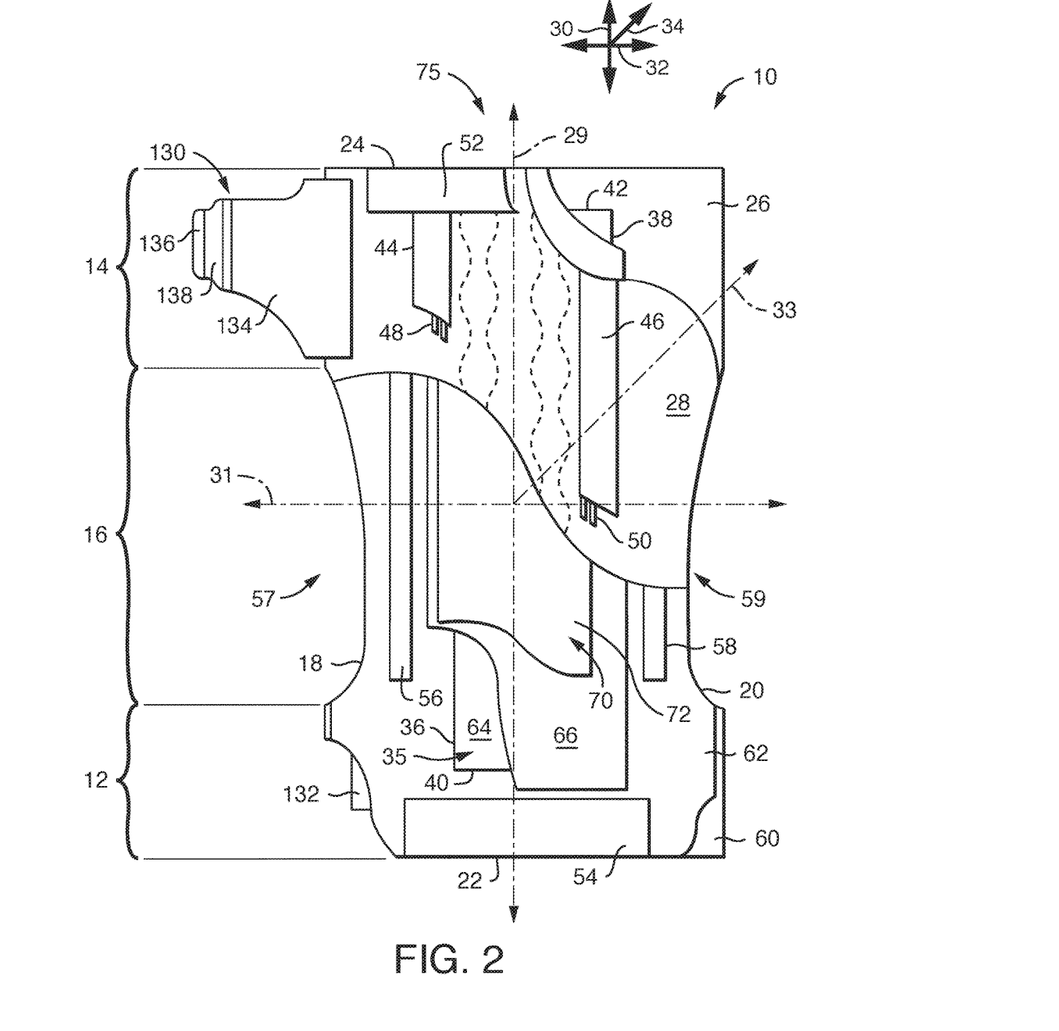
FIG. 2 is a top plan view of the absorbent article of FIG. 1 in an unfastened, stretched, and laid flat condition with the body facing surface of the absorbent article that contact the wearer facing the viewer, portions of the absorbent article being cut away for clarity of illustration.

Referring to FIGS. 1 and 2, a non-limiting example of an absorbent article 10, in this case a diaper, is illustrated. Other absorbent articles include training pants, youth pants, adult incontinence garments, and feminine hygiene articles. While the aspects and illustrations described herein can generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening 23. Portions of the longitudinal side edges, 18 and 20, in the crotch region 16 can generally define leg openings when the absorbent article 10 is worn.

The absorbent article 10 can include a backsheet 26 and a body facing liner 28. In an aspect, the body facing liner 28 can be bonded to the backsheet 26 in a superposed relation by any suitable means such as, but not limited to, adhesives, ultrasonic bonds, thermal bonds, pressure bonds, or other conventional techniques. The backsheet 26 can define a length in a longitudinal direction 30, and a width in the lateral direction 32, which, in the illustrated aspect, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32. The longitudinal axis 29 and the lateral axis 31 can define a horizontal plane. The absorbent article 10 can also have a vertical axis 33 extending in a vertical direction 34. The vertical axis 33 is perpendicular to the horizontal plane defined by the longitudinal axis 29 and the lateral axis 31.

FIG. 2 illustrates the absorbent article 10 with certain portions cut-away for illustrating additional aspects of the absorbent article 10. An absorbent body 35 can be disposed between the backsheet 26 and the body facing liner 28. The absorbent body 35 can have longitudinal edges, 36 and 38, which, in an aspect, can form portions of the longitudinal side edges, 18 and 20, respectively, of the absorbent article 10 and can have opposite end edges, 40 and 42, which, in an aspect, can form portions of the waist edges, 22 and 24, respectively, of the absorbent article 10. In an aspect, the absorbent body 35 can have a length and width that are the same as or less than the length and width of the absorbent article 10. The absorbent article 10 can also include a fluid acquisition layer 70 and a fluid transfer layer 66.

The absorbent article 10 can be configured to contain and/or absorb liquid, solid, and semi-solid body exudates discharged from the wearer. For example, containment flaps, 44 and 46, can be configured to provide a barrier to the lateral flow of body exudates. As illustrated in FIG. 2, each containment flap 44, 46 can include elastic members 48, 50. The elastic members 48, 50 can include one or more elastic strands (two are shown in FIG. 2) that are aligned substantially parallel to the longitudinal axis 29 of the absorbent article 10. The containment flaps 44, 46 are laterally spaced from one another, such that the containment flap 44 is on one side of the longitudinal axis 29 and the containment flap 46 is on an opposite side of the longitudinal axis 29. The containment flaps 44, 46 can be attached to the absorbent article 10 by being bonded to the body facing liner 28. The containment flaps, 44 and 46, can be located laterally inward from the longitudinal side edges, 18, 20 of the absorbent article 10, and can extend longitudinally along the entire length of absorbent article 10 or can extend partially along the length of the absorbent article 10.

To further enhance containment and/or absorption of body exudates, in some aspects the absorbent article 10 can suitably include a rear waist elastic member 52, a front waist elastic member 54, and leg elastic members, 56 and 58, as are known to those skilled in the art. The waist elastic members, 52 and 54, can be attached to the backsheet 26 and/or the body facing liner 28 along the opposite waist edges, 24 and 22, and can extend over part or all of the waist edges, 24 and 22. In an aspect shown in FIG. 2, the rear waist elastic member 52 is attached to the body facing liner 28 and the containment flaps 44, 46 and the front waist elastic member 54 is attached to the backsheet 26. The leg elastic members, 56 and 58, can be attached to the backsheet 26 and/or the body facing liner 28 along the opposite longitudinal side edges, 18 and 20, and positioned in the crotch region 16 of the absorbent article 10.

Additional details regarding each of these elements of the absorbent article 10 described herein can be found below and with reference to the FIGS. 1-5.

The backsheet 26 and/or portions thereof can be breathable and/or liquid impermeable. The backsheet 26 and/or portions thereof can be elastic, stretchable, or non-stretchable. The backsheet 26 can be constructed of a single layer, multiple layers, laminates, spunbond fabrics, films, meltblown fabrics, elastic netting, microporous webs, bonded-carded webs or foams provided by elastomeric or polymeric materials. In an aspect, for example, the backsheet 26 can be constructed of a microporous polymeric film, such as polyethylene or polypropylene.

In an aspect, the backsheet 26 can be a single layer of a liquid impermeable material. In an aspect, the backsheet 26 can be suitably stretchable, and more suitably elastic, in at least the lateral or circumferential direction 32 of the absorbent article 10. In an aspect, the backsheet 26 can be stretchable, and more suitably elastic, in both the lateral 32 and the longitudinal 30 directions. In an aspect, the backsheet 26 can be a multi-layered laminate in which at least one of the layers is liquid impermeable. In an aspect, the backsheet 26 can be a two layer construction, including an outer layer material 60 and an inner layer material 62 that can be bonded together such as by a laminate adhesive. Suitable laminate adhesives can be applied continuously or intermittently as beads, a spray, parallel swirls, or the like, but it is to be understood that the inner layer 62 can be bonded to the outer layer 60 by other bonding methods, including, but not limited to, ultrasonic bonds, thermal bonds, pressure bonds, or the like.

The outer layer 60 of the backsheet 26 can be any suitable material and can be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 60 of a backsheet 26 can be a 20 gsm spunbond polypropylene non-woven web. The outer layer 60 can also be constructed of the same materials from which the body facing liner 28 can be constructed as described herein.

The liquid impermeable inner layer 62 of the backsheet 26 (or the liquid impermeable backsheet 26 where the backsheet 26 is of a single-layer construction) can be either vapor permeable (i.e., "breathable") or vapor impermeable. The liquid impermeable inner layer 62 (or the liquid impermeable backsheet 26 where the backsheet 26 is of a single-layer construction) can be manufactured from a thin plastic film, although other liquid impermeable materials can also be used. The liquid impermeable inner layer 62 (or the liquid impermeable backsheet 26 where the backsheet 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 62 (or the liquid impermeable backsheet 26 where the backsheet 26 is of a single-layer construction) can be a printed 19 gsm Berry Plastics XP-8695H film or equivalent commercially available from Berry Plastics Corporation, Evansville, Ind., U.S.A.

Where the backsheet 26 is of a single layer construction, it can be embossed and/or matte finished to provide a more cloth-like texture or appearance. The backsheet 26 can permit vapors to escape from the absorbent article 10 while preventing liquids from passing through. A suitable liquid impermeable, vapor permeable material can be composed of a microporous polymer film or a non-woven material that has been coated or otherwise treated to impart a desired level of liquid impermeability.

The absorbent body 35 can be suitably constructed to be generally compressible, conformable, pliable, non-irritating to the wearer's skin and capable of absorbing and retaining liquid body exudates. The absorbent body 35 can be manufactured in a wide variety of sizes and shapes (for example, rectangular, trapezoidal, T-shape, I-shape, hourglass shape, etc.) and from a wide variety of materials. The size and the absorbent capacity of the absorbent body 35 should be compatible with the size of the intended wearer (infants to adults) and the liquid loading imparted by the intended use of the absorbent article 10. The absorbent body 35 can have a length and width that can be less than or equal to the length and width of the absorbent article 10. The absorbent body 35 can have two surfaces such as a wearer facing surface 64 and a garment facing surface (not shown). Edges, such as longitudinal side edges, 36 and 38, and such as front and back end edges, 40 and 42, can connect the two surfaces.

In an aspect, the absorbent body 35 can include of a web material of hydrophilic fibers, cellulosic fibers (e.g., wood pulp fibers), natural fibers, synthetic fibers, woven or non-woven sheets, scrim netting or other stabilizing structures, superabsorbent material, binder materials, surfactants, selected hydrophobic and hydrophilic materials, pigments, lotions, odor control agents or the like, as well as combinations thereof. In an aspect, the absorbent body 35 can be a matrix of cellulosic fluff and superabsorbent material. In an aspect, the absorbent body 35 can be constructed of a single layer of materials, or in the alternative, can be constructed of two or more layers of materials.

Various types of wettable, hydrophilic fibers can be used in the absorbent body 35. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers that have been hydrophilized by suitable means. The fibers can be hydrophilized, for example, by treatment with a surfactant, treatment with silica, treatment with a material that has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an aspect, the absorbent body 35 can be free of superabsorbent material.

The absorbent body 35 can be superposed over the inner layer 62 of the backsheet 26, extending laterally between the leg elastic members, 56, 58, and can be bonded to the inner layer 62 of the backsheet 26, such as by being bonded thereto with adhesive. However, it is to be understood that the absorbent body 35 can be in contact with, and not bonded with, the backsheet 26 and remain within the scope of this disclosure. In an aspect, the backsheet 26 can be composed of a single layer and the absorbent body 35 can be in contact with the single layer of the backsheet 26. In an aspect, a layer, such as but not limited to, a fluid transfer layer 66, can be positioned between the absorbent body 35 and the backsheet 26.

In various aspects an absorbent article 10 can be constructed without a fluid transfer layer 66. In various aspects the absorbent article 10 can have a fluid transfer layer 66. In an aspect, the fluid transfer layer 66 can be in contact with the absorbent body 35. In an aspect, the fluid transfer layer 66 can be bonded to the absorbent body 35. Bonding of the fluid transfer layer 66 to the absorbent body 35 can occur via any means known to one of ordinary skill, such as, but not limited to, adhesives. In an aspect, a fluid transfer layer 66 can be positioned between the body facing liner 28 and the absorbent body 35. In an aspect, a fluid transfer layer 66 can completely encompass the absorbent body 35 and can be sealed to itself. In an aspect a fluid transfer layer 66 can be composed of separate sheets of material that can be utilized to partially or fully encompass the absorbent body 35 and that can be sealed together using a sealing means such as, but not limited to, an ultrasonic bonder or other thermochemical bonding means or the use of an adhesive. In an aspect, the fluid transfer layer 66 can be in contact with and/or bonded with the wearer facing surface 64 of the absorbent body 35.

The fluid transfer layer 66 can be pliable, less hydrophilic than the absorbent body 35, and sufficiently porous to thereby permit liquid body exudates to penetrate through the fluid transfer layer 66 to reach the absorbent body 35. In an aspect, the fluid transfer layer 66 can have sufficient structural integrity to withstand wetting thereof and of the absorbent body 35. In an aspect, the fluid transfer layer 66 can be constructed from a single layer of material or it can be a laminate constructed from two or more layers of material. In an aspect, the fluid transfer layer 66 can include, but is not limited to, natural and synthetic fibers such as, but not limited to, polyester, polypropylene, acetate, nylon, polymeric materials, cellulosic materials and combinations thereof. In an aspect, a fluid transfer layer 66 can include spunbond and/or meltblown materials. In an aspect, the fluid transfer layer 66 can be a laminate of a meltblown nonwoven material having fine fibers laminated to at least one spunbond nonwoven material layer having coarse fibers. In such an aspect, the fluid transfer layer 66 can be a spunbond-meltblown ("SM") material, while in other aspects, the fluid transfer layer 66 can be a spunbond-meltblown-spunbond ("SMS") material. In various aspects, the fluid transfer layer 66 can be hydrophilic. In various aspects, the fluid transfer layer 66 can be hydrophobic and can be treated in any manner known in the art to be made hydrophilic. In an aspect, the fluid transfer layer 66 can have a longitudinal length the same as, greater than, or less than the longitudinal length of the absorbent body 35.

In various aspects the absorbent article 10 can have a fluid acquisition layer 70. The acquisition layer 70 can help decelerate and diffuse surges or gushes of liquid body exudates penetrating the body facing liner 28. In an aspect, the acquisition layer 70 can be positioned between the body facing liner 28 and the backsheet 26. In an aspect, the acquisition layer 70 can be positioned between the body facing liner 28 and the absorbent body 35 to take in and distribute body exudates for absorption by the absorbent body 35. In an aspect, the acquisition layer 70 can be positioned between the body facing liner 28 and a fluid transfer layer 66 if a fluid transfer layer 66 is present.

In an aspect, the acquisition layer 70 can be in contact with and/or bonded with the body facing liner 28. In an aspect in which the acquisition layer 70 is bonded with the body facing liner 28, bonding of the acquisition layer 70 to the body facing liner 28 can occur through the use of an adhesive and/or point fusion bonding, but is not limited to such methods of bonding. For example, the body facing liner 28 could be bonded to the acquisition layer 70 by hydroentangling the body facing liner 28 with the acquisition layer 70. The point fusion bonding can be selected from, but is not limited to, ultrasonic bonding, pressure bonding, thermal bonding, and combinations thereof. In an aspect, the point fusion bonding can be provided in any pattern as deemed suitable. As an example, the body facing liner 28 can be bonded to the acquisition layer 70 at a range of 1%-90%. The percentage of bonding between the body facing liner 28 and the acquisition layer 70 can be measured by calculating the area of bonded material between the body facing liner 28 and the acquisition layer 70 and dividing by the area of overlap between the body facing liner 28 and the acquisition layer 70 as viewed from the vertical direction 34 perpendicular to both the longitudinal and lateral directions 30, 32, as in a dimension that is perpendicular to the plane of the body facing liner 28 when the body facing liner 28 is laid flat.

The acquisition layer 70 can be rectangular in shape, or can be any other shape. The acquisition layer 70 can have any longitudinal length dimension as deemed suitable. For example, the acquisition layer 70 can have a longitudinal length shorter than, the same as, or longer than the longitudinal length of the absorbent body 35. In an aspect, the acquisition layer 70 can have any length such that the acquisition layer 70 can be coterminous with the waist edges, 22 and 24, of the absorbent article 10. In an aspect, the longitudinal length of the acquisition layer 70 can be the same as the longitudinal length of the absorbent body 35. In such an aspect, the midpoint of the longitudinal length of the acquisition layer 70 can substantially align with the midpoint of the longitudinal length of the absorbent body 35.

In an aspect, the longitudinal length of the acquisition layer 70 can be shorter than the longitudinal length of the absorbent body 35. In such an aspect, the acquisition layer 70 can be positioned at any desired location along the longitudinal length of the absorbent body 35. As an example of such an aspect, the absorbent article 10 can contain a target area where repeated liquid surges typically occur in the absorbent article 10. The particular location of a target area can vary depending on the age and gender of the wearer of the absorbent article 10. For example, males tend to urinate further toward the front waist region 12 of the absorbent article 10 and the target area can be phased forward within the absorbent article 10. For example, the target area for a male wearer can be positioned about 2 ¾" forward of the longitudinal midpoint of the absorbent body 35 and can have a length of about ±3" and a width of about ±2". The female target area can be located closer to the center of the crotch region 16 of the absorbent article 10. For example, the target area for a female wearer can be positioned about 1" forward of the longitudinal midpoint of the absorbent body 35 and can have a length of about ±3" and a width of about ±2". As a result, the relative longitudinal placement of the acquisition layer 70 within the absorbent article 10 can be selected to best correspond with the target area of either or both categories of wearers.

In an aspect, the absorbent article 10 can contain a target area centered within the crotch region 16 of the absorbent article 10 with the premise that the absorbent article 10 would be worn by a female wearer. The acquisition layer 70, therefore, can be positioned along the longitudinal length of the absorbent article 10 such that the acquisition layer 70 can be substantially aligned with the target area of the absorbent article 10 intended for a female wearer. Alternatively, the absorbent article 10 can contain a target area positioned between the crotch region 16 and the front waist region 12 of the absorbent article 10 with the premise that the absorbent article 10 would be worn by a male wearer. The acquisition layer 70, therefore, can be positioned along the longitudinal length of the absorbent article 10 such that the acquisition layer 70 can be substantially aligned with the target area of the absorbent article 10 intended for a male wearer. In an aspect, the acquisition layer 70 can have a size dimension that is the same size dimension as the target area of the absorbent article 10 or a size dimension greater than the size dimension of the target area of the absorbent article 10. In an aspect, the acquisition layer 70 can be in contact with and/or bonded with the body facing liner 28 at least partially in the target area of the absorbent article 10.

In various aspects, the acquisition layer 70 can have a longitudinal length shorter than, the same as, or longer than, the longitudinal length of the absorbent body 35. In an aspect in which the absorbent article 10 is a diaper, the acquisition layer 70 can have a longitudinal length from about 120, 130, 140, 150, 160, 170, or 180 mm to about 200, 210, 220, 225, 240, 260, 280, 300, 310 or 320 mm. In such an aspect, the acquisition layer 70 can be shorter in longitudinal length than the longitudinal length of the absorbent body 35 and can be phased from the front end edge 40 of the absorbent body 35 a distance of from about 15, 20, or 25 mm to about 30, 35 or 40 mm. In an aspect in which the absorbent article 10 can be a training pant or youth pant, the acquisition layer 70 can have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an aspect, the acquisition layer 70 can have a longitudinal length shorter than the longitudinal length of the absorbent body 35 and can be phased a distance of from about 25, 30, 35 or 40 mm to about 45, 50, 55, 60, 65, 70, 75, 80 or 85 mm from the front end edge 40 of the absorbent body 35. In an aspect in which the absorbent article 10 is an adult incontinence garment, the acquisition layer 70 can have a longitudinal length from about 200, 210, 220, 230, 240, or 250 mm to about 260, 270, 280, 290, 300, 320, 340, 360, 380, 400, 410, 415, 425, or 450 mm. In such an aspect, the acquisition layer 70 can have a longitudinal length shorter than the longitudinal length of the absorbent body 35 and the acquisition layer 70 can be phased a distance of from about 20, 25, 30 or 35mm to about 40, 45, 50, 55, 60, 65, 70 or 75 mm from the front end edge 40 of the absorbent body 35.

The acquisition layer 70 can have any width as desired. The width of the acquisition layer 70 can vary dependent upon the size and shape of the absorbent article 10 within which the acquisition layer 70 will be placed. The acquisition layer 70 can have a width smaller than, the same as, or larger than the width of the absorbent body 35. Within the crotch region 16 of the absorbent article 10, the acquisition layer 70 can have a width smaller than, the same as, or larger than the width of the absorbent body 35.

The acquisition layer 70 can have a body facing surface and a garment facing surface. The acquisition layer 70 can have at least one aperture or a plurality of apertures (not shown). In some aspects, the apertures can extend from the body facing surface of the acquisition layer 70 to the garment facing surface of the acquisition layer 70. The plurality of apertures can be in a pattern.

The body facing liner 28 of the absorbent article 10 can overlay the absorbent body 35 and the backsheet 26 and can isolate the wearer's skin from liquid waste retained by the absorbent body 35. In various aspects, a fluid transfer layer 66 can be positioned between the body facing liner 28 and the absorbent body 35. In various aspects, an acquisition layer 70 can be positioned between the body facing liner 28 and the absorbent body 35 or a fluid transfer layer 66, if present. In various aspects, the body facing liner 28 can be bonded to the acquisition layer 70, or to the fluid transfer layer 66 if no acquisition layer 70 is present, via adhesive and/or by a point fusion bonding. The point fusion bonding can be selected from ultrasonic, thermal, pressure bonding, and combinations thereof.

In an aspect, the body facing liner 28 can extend beyond the absorbent body 35 and/or a fluid transfer layer 66, and/or an acquisition layer 70 to overlay a portion of the backsheet 26 and can be bonded thereto by any method deemed suitable, such as, for example, by being bonded thereto by adhesive, to substantially enclose the absorbent body 35 between the backsheet 26 and the body facing liner 28. The body facing liner 28 can be narrower than the backsheet 26, but it is to be understood that the body facing liner 28 and the backsheet 26 can be of the same dimensions. It is also contemplated that the body facing liner 28 not extend beyond the absorbent body 35 and/or not be secured to the backsheet 26. It is further contemplated that the body facing liner 28 can be composed of more than one segment of material. The body facing liner 28 can be of different shapes, including rectangular, hourglass, or any other shape. The body facing liner 28 can be suitably compliant, soft feeling, and non-irritating to the wearer's skin and can be the same as or less hydrophilic than the absorbent body 35 to permit body exudates to readily penetrate through to the absorbent body 35 and provide a relatively dry surface to the wearer.

The body facing liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the body facing liner 28. The body facing liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The body facing liner 28 need not be a unitary layer structure, and thus, can include more than one layer of fabrics, films, and/or webs, as well as combinations thereof. For example, the body facing liner 28 can include a support layer and a projection layer that can be hydroentangled.

For example, the body facing liner 28 can include meltblown or spunbond web of polyolefin fibers. Alternatively, the body facing liner 28 can be a bonded-carded web composed of natural and/or synthetic fibers. The body facing liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire body facing liner 28 or it can be selectively applied to particular sections of the body facing liner 28.

In an aspect, a body facing liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, and end-to-end can be used without departing from the scope of this disclosure. In an aspect, a body facing liner 28 can be a spunbond substrate with a basis weight from about 10 or 12 to about 15 or 20 gsm. In an aspect, a body facing liner 28 can be a 12 gsm spunbond-meltblown-spunbond substrate having 10% meltblown content applied between the two spunbond layers.

Although the backsheet 26 and body facing liner 28 can include elastomeric materials, it is contemplated that the backsheet 26 and the body facing liner 28 include materials that are generally non-elastomeric. In an aspect, the body facing liner 28 can be stretchable, and more suitably elastic. In an aspect, the body facing liner 28 can be suitably stretchable and more suitably elastic in at least the lateral or circumferential direction of the absorbent article 10. In other aspects, the body facing liner 28 can be stretchable, and more suitably elastic, in both the lateral and the longitudinal directions 32, 30, respectively.

In an aspect, containment flaps, 44, 46, can be secured to the body facing liner 28 of the absorbent article 10 in a generally parallel, spaced relation with each other laterally inward of the leg openings to provide a barrier against the flow of body exudates. In an aspect, the containment flaps, 44, 46, can extend longitudinally from the front waist region 12 of the absorbent article 10, through the crotch region 16 to the back waist region 14 of the absorbent article 10. The containment flaps 44, 46 can be bonded to the body facing liner 28 with adhesive or other means as are known in the art. Alternatively, each containment flap 44, 46 can be bonded to other components of the absorbent article 10 other than the body facing liner 28, including, but not limited to, the backsheet 26.

The containment flaps, 44 and 46, can be constructed of a fibrous material that can be similar to the material forming the body facing liner 28. Other conventional materials, such as polymer films, can also be employed. Each containment flap, 44 and 46, can include flap elastics, such as flap elastics 48 and 50, respectively. Suitable elastic materials for the flap elastic, 48 and 50, can include sheets, strands or ribbons of natural rubber, synthetic rubber, or thermoplastic elastomeric materials. The flap elastics, 48 and 50, as illustrated, can have two strands of elastomeric material extending longitudinally along the containment flaps, 44 and 46, in generally parallel, spaced relation with each other. The elastic strands can be within the containment flaps, 44 and 46, while in an elastically contractible condition such that contraction of the strands gathers and shortens the containment flaps, 44 and 46. As a result, the elastic strands can bias the containment flaps, 44 and 46, toward a position spaced from a position of where the containment flaps, 44 and 46, are bonded to absorbent article 10 such that a portion of the containment flaps, 44 and 46, can extend away from the body facing liner 28 in a generally upright orientation of the containment flaps, 44 and 46, especially in the crotch region 16 of the absorbent article 10, when the absorbent article 10 is fitted on the wearer. The containment flaps, 44 and 46, can be connected to the flap elastics, 48 and 50, by partially doubling a portion of the containment flap, 44 and 46, material back upon itself by an amount that can be sufficient to enclose the flap elastics, 48 and 50. It is to be understood, however, that the containment flaps, 44 and 46, can have any number of strands of elastomeric material and can also be omitted from the absorbent article 10 without departing from the scope of this disclosure.

Leg elastic members 56, 58 can be secured to the backsheet 26, such as by being bonded thereto by laminate adhesive, generally laterally inward of the longitudinal side edges, 18 and 20, of the absorbent article 10. The leg elastic members 56, 58 can form elasticized leg cuffs 57, 59, respectively, that further help to contain body exudates. In an aspect, the leg elastic members 56, 58 can be disposed between the inner layer 62 and outer layer 60 of the backsheet 26 or between other layers of the absorbent article 10. The leg elastic members 56, 58 can be a single elastic member as illustrated in the figures herein, or each leg elastic member 56, 58 can include more than one elastic member. A wide variety of elastic materials can be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

In an aspect, the absorbent article 10 can include a fastener system. The fastener system can include one or more back fasteners 130 and one or more front fasteners 132. Portions of the fastener system can be included in the front waist region 12, back waist region 14, or both. The fastener system can be configured to secure the absorbent article 10 about the waist of the wearer and maintain the absorbent article 10 in place during use. In an aspect, the back fasteners 130 can include one or more materials bonded together to form a composite ear as is known in the art. For example, the composite fastener can be composed of a stretch component 134, a nonwoven carrier or hook base 136, and a fastening component 138.

In an aspect, the absorbent article 10 can have waist elastic members, 52 and 54, which can be formed of any suitable elastic material. The waist elastic member 52 can be in a rear waist region 14 of the absorbent article 10 and the waist elastic member 54 can be in a front waist region 12 of the absorbent article 10. Suitable elastic materials for the waist elastic members 52, 54 can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 52 and 54, can be omitted from the absorbent article 10 without departing from the scope of this disclosure.

Figure 3:
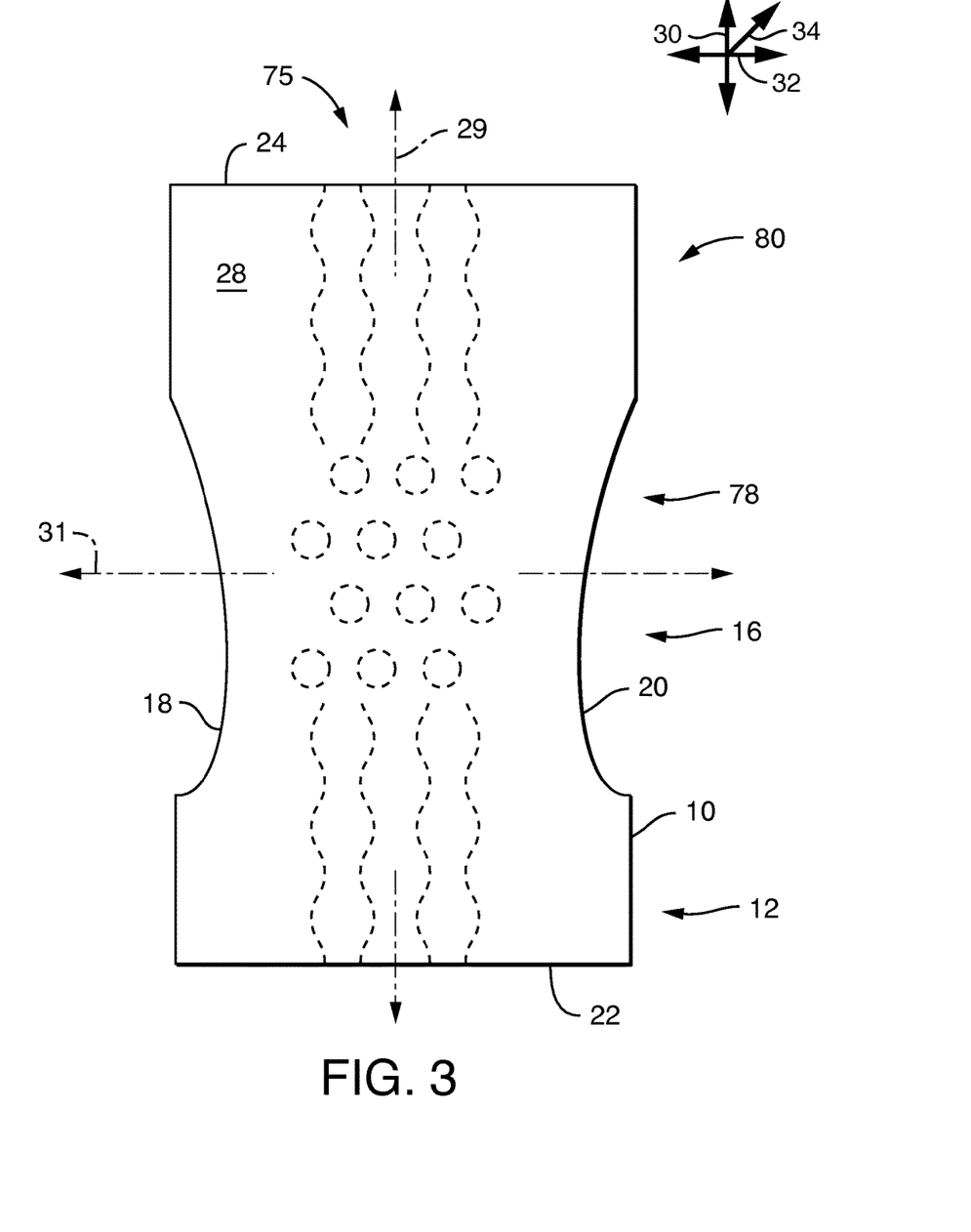
FIG. 3 is a top plan view of a body facing liner of the absorbent article of FIG. 1, the liner having a plurality of embossed features, where the absorbent article is designed for use by females.
Figure 4:
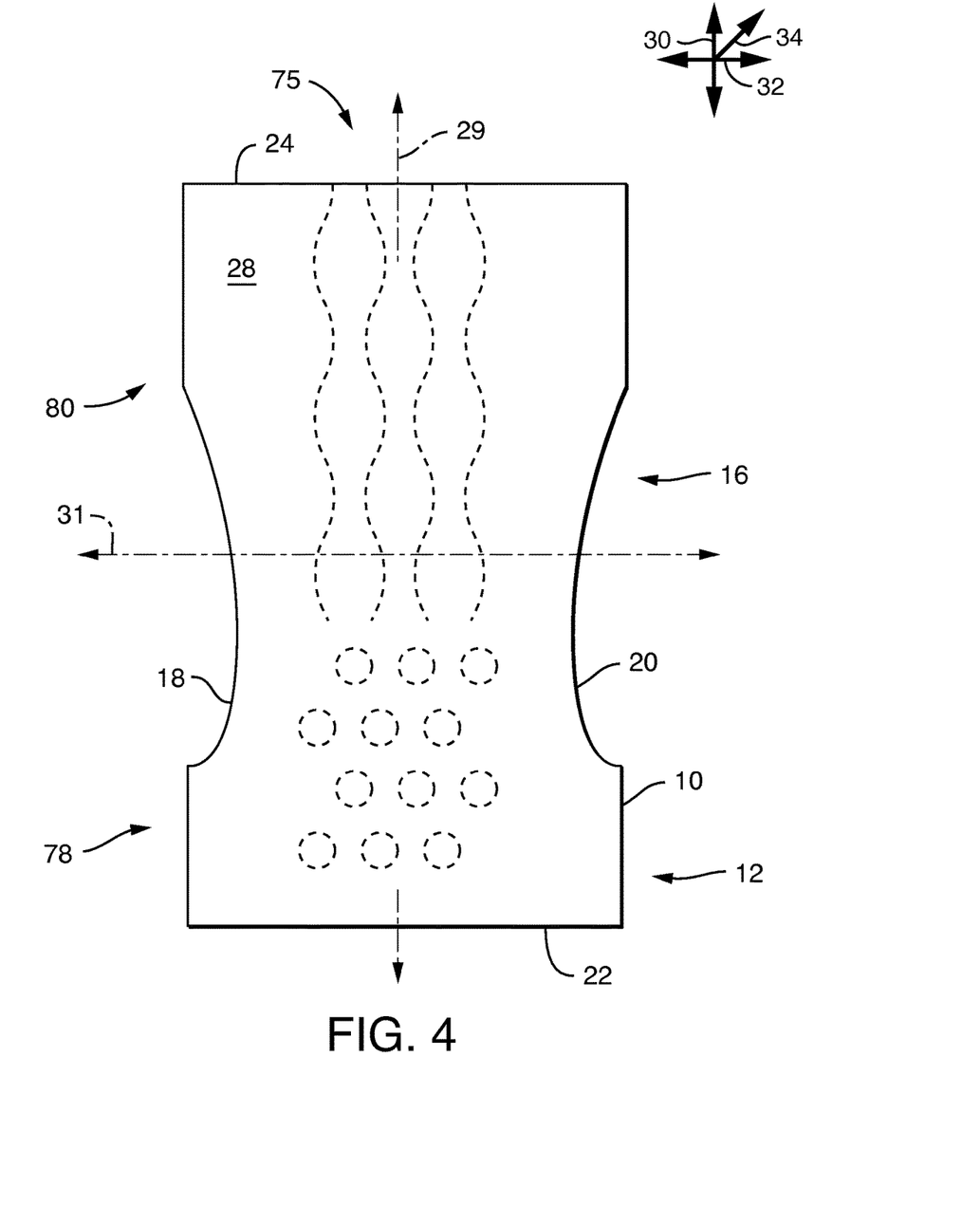
FIG. 4 is a top plan view of an alternative body facing liner of the absorbent article of FIG. 1, the liner having a plurality of embossed features, where the absorbent article is designed for use by males.

The body facing liner can exhibit a variety of embossing patterns that bond the body facing liner 28 to the acquisition layer 70 or to any other layer adjacent the body facing liner 28. The embossing pattern 75 can be of various shapes and sizes, and some portions of the embossing pattern 75 can be different from the size and/or shape of other portions of the embossing pattern 75. For example, portions of the embossing pattern 75 can be circular in shape, as shown in the exemplary aspect in FIGS. 3 and 4. Portions of the embossing pattern 75 can alternatively be elliptical in shape or be of any other suitable shape, including shapes other than circular and elliptical, including, but not limited to, regular and irregular polygons (regular and irregular triangles, regular and irregular rectangles, regular and irregular pentagons, etc.), and irregular shapes. Such shapes are generally referred to as closed shapes. Portions of the embossing pattern 75 can alternatively be straight lines, wavy lines (as shown in the exemplary aspects of FIGS. 2-4), parallel lines, or any other suitable lines, shapes, or combinations, generally referred to as open shapes. As shown in FIGS. 3 and 4, the embossing pattern 75 can be a combination of different lines and shapes.

As shown in the exemplary aspects of FIGS. 3 and 4, the embossing pattern 75 can be described as having a target zone 78 and having a channel zone 80. The target zone 78 has a bonding pattern different from the bonding pattern of the channel zone 80. The target zone 78 is intended to be the most probable location for a urine insult. Because of anatomical differences, the target zone 78 in an absorbent article 10 intended for use by males is located differently from the target zone 78 in an absorbent article 10 intended for use by females. As shown in the exemplary aspects of FIGS. 3 and 4, the target zone 78 is located primarily in the crotch region 16 for an absorbent article 10 intended for use by girls (FIG. 3) and primarily in the front waist region 12 for an absorbent article 10 intended for use by boys (FIG. 4).

The size of portions of the embossing pattern 75 can also vary. For example, in an exemplary aspect, a portion that is circular in shape can have a diameter in the range of 1.0 mm to 100.0 mm, preferably in the range of 4.0 mm to 50.0 mm, and more preferably in the range of 6.0 mm to 20.0 mm.

The embossing pattern 75 can form a plurality of rows and a plurality of columns. The rows can extend in a direction parallel to the lateral axis 31 and can be offset from one another in a direction parallel to the longitudinal axis 29. The columns can extend in a direction parallel to the longitudinal axis 29 and can be offset from one another in a direction parallel to the lateral axis 31. Of course, it is contemplated that the rows and columns are not limited to such orientations. In an aspect, the number of rows can be selected from the range of 1-50, preferably from the range of 4-30, and more preferably from the range of 6-20. In one aspect, the number of columns can be selected from the range of 1-25, preferably from the range of 2-20, and more preferably from the range of 3-15. The embossing pattern 75, including the amount and the positioning of the rows and columns, can correspond to features in the body facing liner 28, as will be discussed in further detail below. The rows and the columns can be configured such that there is phasing between adjacent rows and/or adjacent columns of the embossing pattern such that adjacent rows are not aligned in the longitudinal direction 30 and adjacent columns are not aligned in the lateral direction 32. Phasing of the rows and/or columns can provide the advantages of more dense embossing patterns 75. Additionally, the phasing of the rows and/or columns can provide for higher tensile strengths of the body facing liner 28 in both the longitudinal 30 and lateral 32 directions compared to similar patterns that do not have phased rows and/or columns.

The target zone 78 and the channel zone 80 each have a bond pattern, and each of those bond patterns has a bond density, which is the ratio of bonded area to unbonded area. In one aspect, the bond density of the target zone bond pattern is less than the bond density of the channel zone bond pattern. In another aspect, the bond density of the target zone bond pattern is greater than the bond density of the channel zone bond pattern. In addition, the bond density can vary along the longitudinal direction 30.

In other aspects, the embossing patterns 75 can be arranged irrespective of the structure of the absorbent article 10, or the embossing patterns 75 can be registered with respect to one or both of the longitudinal axis 29 and the transverse axis 31. In another aspect, one or both of the fluid acquisition layer 70 and the body facing liner 28 can be pigmented to highlight or mask the embossing pattern 75.

The embossing patterns 75 depicted in the aspects shown in FIGS. 2-4 provide advantages in the distribution of exudates in an absorbent article 10. For example, when exudates transfer through the body facing liner 28 toward the absorbent body 35, the exudates can contact the body facing surface 72 of the acquisition layer 70. The acquisition layer 70 can accept the exudates and transfer the exudates to other layers of the absorbent article 10, such as a fluid transfer layer 66 and/or the absorbent body 35. If exudates are concentrated in any particular area of the body facing surface of the acquisition layer 70, the embossing pattern 75 can provide reduced resistance for the exudates to flow to spread throughout the acquisition layer 70. Such a configuration is believed to increase the effectiveness of distribution of exudates in the acquisition layer 70 or other appropriate layer. A more effective distribution of exudates in the acquisition layer 70 or other appropriate layer can provide an increase in the effectiveness of the absorbent body 35, which in turn can reduce the potential for skin irritation of the wearer by reducing the amount of exudates that can return to the body facing liner 28. Also, the increase in distribution of the exudates throughout the acquisition layer 70 or other appropriate layer, and in turn an increase in the effectiveness of the absorbent body 35, can assist in reducing the likelihood that the gasketing of the absorbent article 10 can be compromised.

The embossing pattern of the target zone 78 is developed to convey both actual intake and the perception of intake. The embossing pattern of the channel zone 80 is developed to convey both actual and the perception of distribution of fluid.

In an aspect, the acquisition layer 70 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an aspect, the acquisition layer 70 can be formed from a material that is substantially hydrophobic, such as a nonwoven web composed of polypropylene, polyethylene, polyester, and the like, and combinations thereof.

The embossing pattern 75 can be formed in the body facing liner 28, the acquisition layer 70, or other suitable layer using various manufacturing techniques. For example, an embossing pattern 75 can be formed in the body facing liner 28 using in part an embossing roller 85 (see FIG. 5). The creation of the embossing pattern 75 can be done off the machine line forming absorbent articles 10, or can be done in-line with the machine line forming absorbent articles 10.

For example, to bond the body facing liner 28 to the acquisition layer 70, a web of body facing liner material is provided in face-to-face relation with a web of acquisition layer material. The combined webs are then contacted by an embossing roller 85 having an embossing pattern 75. The embossing pattern 75 is thereby applied to the combined webs, causing them to be bonded with the embossing pattern 75.

Figure 5:
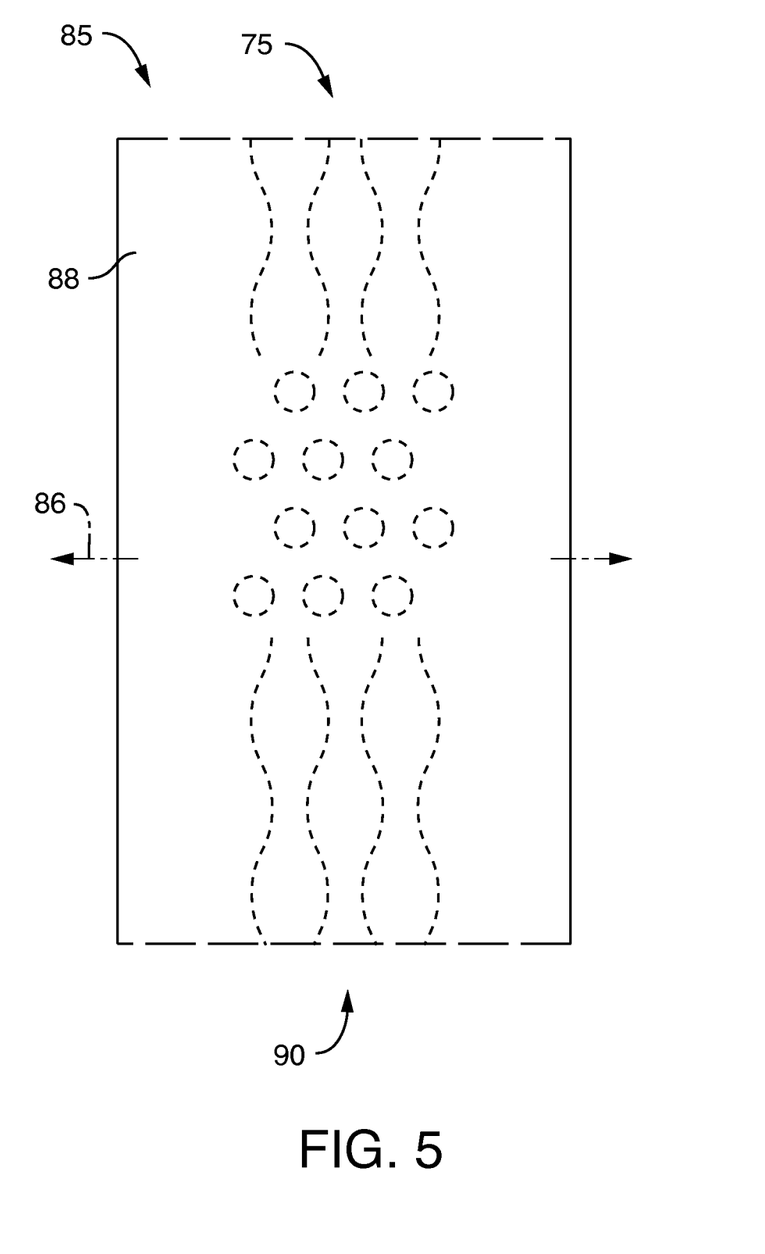
FIG. 5 is a flattened top plan schematic view of the surface of an embossing roller used online in the production of the absorbent article of FIG. 1.

As illustrated in FIG. 5, the embossing roller 85 has a lateral axis 86 and a circumferential surface 88. The circumferential surface 88 has a circumferential lane 90. The circumferential lane 90 has azimuthally-alternating target zone and channel zone embossing patterns. The use of a single circumferential lane allows the bonding to be performed online, which streamlines the manufacturing process for the absorbent articles 10. To achieve differentiation between male and female products, the application of the embossing patterns can be phased with respect to the web such that target zones 78 and channel zones 80 are positioned differently in male and female products. This phasing can be accomplished by altering the positioning of the embossing roller 85 with respect to the web, by altering the registration of the web with respect to the rest of the absorbent articles 20, or by any other suitable process or adjustment.

In contrast, creating the embossing pattern 75 off-line allows cutting to be completed at various speeds, including speeds that can be slower than the machine-line forming the absorbent articles 10, which can allow more precise cutting. Furthermore, the production of the embossing pattern 75 can be done in the same process steps or in separate steps. Off-line embossing is more likely if the web to be embossed was a single layer, or is a multiple layer web where the body facing liner 28 and acquisition layer 70 have the same width and length in the end product. An advantage of embossing the web off-line in this situation is that it can be run at higher machine speeds than an absorbent article assembly line. Running off-line also reduces the complexity and down time of the absorbent article assembly line.

Figure 6:
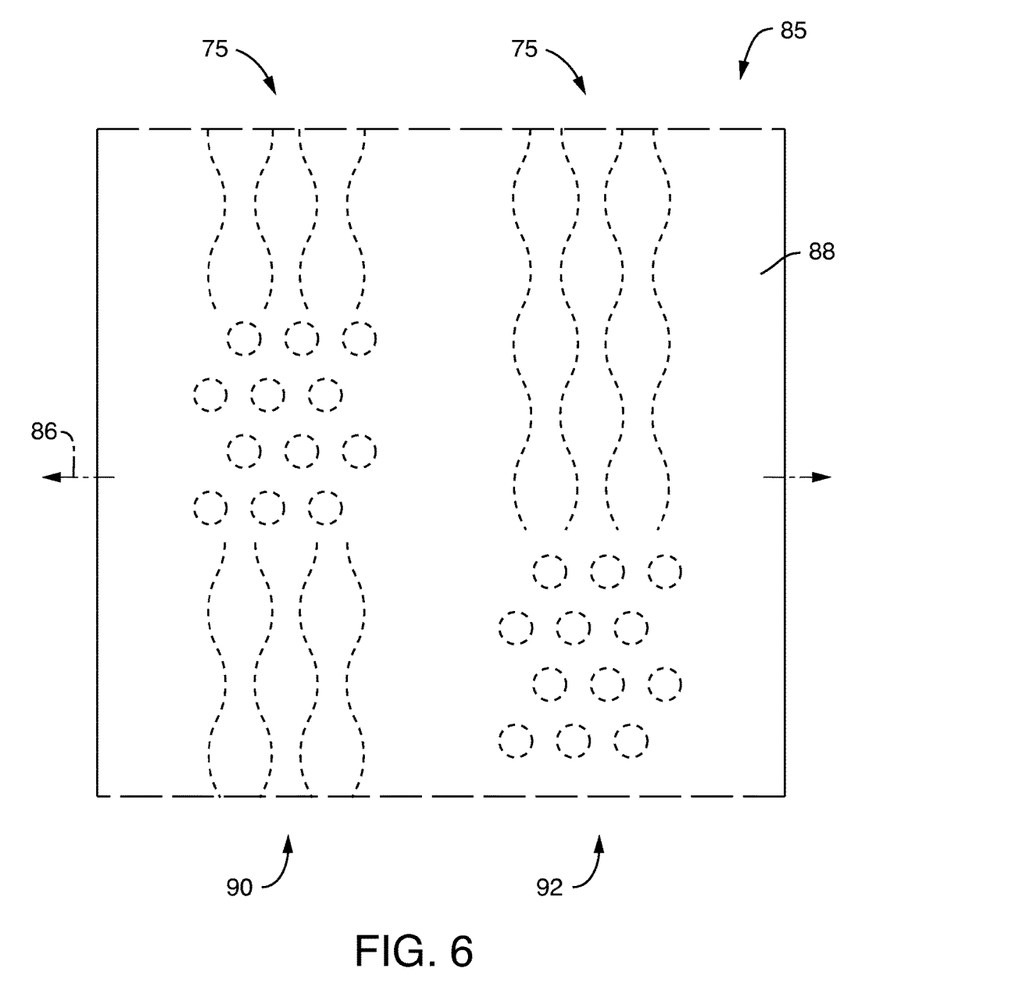
FIG. 6 is a flattened top plan schematic view of the surface of an embossing roller used offline in the production of the absorbent article of FIG. 1.

As illustrated in FIG. 6, the embossing roller 85 has a lateral axis 86 and a circumferential surface 88. The circumferential surface 88 is divided into at least first and second circumferential lanes 90, 92. Each circumferential lane 90, 92 has azimuthally-alternating target zone and channel zone embossing patterns. The second circumferential lane 92 can be azimuthally offset from the first circumferential lane 90. In other aspects, the embossing roller 85 can include third, fourth, or additional circumferential lanes. The target zone and channel zone embossing patterns of the first circumferential lane 90 can be identical to the target zone and channel zone embossing patterns of the second circumferential lane 92, or the target zone and channel zone embossing patterns of the first and second circumferential lanes 90, 92 can be different from each other. Multiple and varying embossing patterns in the lateral direction allows the deckle (web width) to be more completely filled Because each absorbent article size or type has a particular ratio of male to female users, the least amount of waste is produced by embossing in the correct ratio of male to female bonding patterns.

The embossing pattern 75 can be of various shapes and sizes, and some portions of the embossing pattern 75 can be different from the size and/or shape of other portions of the embossing pattern 75. For example, portions of the embossing pattern 75 can be circular in shape, as shown in the exemplary aspect in FIGS. 5 and 6. Portions of the embossing pattern 75 can alternatively be elliptical in shape or be of any other suitable shape, including shapes other than circular and elliptical, including, but not limited to, regular and irregular polygons (regular and irregular triangles, regular and irregular rectangles, regular and irregular pentagons, etc.), and irregular shapes. Such shapes are generally referred to as closed shapes. Portions of the embossing pattern 75 can alternatively be straight lines, wavy lines (as shown in the exemplary aspect of FIGS. 5 and 6), parallel lines, or any other suitable lines, shapes, or combinations, generally referred to as open shapes. As shown in FIGS. 5 and 6, the embossing pattern 75 can be a combination of different lines and shapes.

The target zone 78 and the channel zone 80 each have a bond pattern, and each of those bond patterns had a bond density, which is the ratio of bonded area to unbonded area. In one aspect, the bond density of the target zone bond pattern is less than the bond density of the channel zone bond pattern. In another aspect, the bond density of the target zone bond pattern is greater than the bond density of the channel zone bond pattern. In addition, the bond density can vary along the longitudinal direction 30.

After the combination web is embossed, the combined web can be cut or otherwise separated as known in the art into individual body facing liner 28/acquisition layer 70 combinations to be used in assembling an absorbent article 10. Each of these body facing liner 28/acquisition layer 70 combinations has a front waist region 12 and a crotch region 16. The cutter or other tool used for separation can be adjusted with respect to the alignment of the embossing roller 85 such that a portion of the body facing liner 28/acquisition layer 70 combinations has the target zone 78 in the front waist region 12 (e.g., FIG. 4), and another portion of the body facing liner 28/acquisition layer 70 combinations has the target zone 78 in the crotch region 16 (e.g., FIG. 3).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular aspects of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A method for manufacturing an absorbent article having a body facing liner, a backsheet coupled to the body facing liner, an absorbent body positioned between the body facing liner and the backsheet, and a fluid acquisition layer having a body facing surface and a garment facing surface, the fluid acquisition layer being positioned between the body facing liner and the backsheet, the method comprising:

providing a web of body facing liner material in face-to-face relation to a web of fluid acquisition layer material;

bonding the body facing liner material to the fluid acquisition layer material using an embossing roller, wherein the embossing roller has an axis and a circumferential surface having a circumferential lane, the circumferential lane having alternating target zone and channel zone embossing patterns;

embossing the body facing liner material and fluid acquisition layer material together to produce a web of bonded body facing liner material and fluid acquisition layer material having alternating target zone and channel zone embossing patterns; and separating the web of bonded body facing liner material and fluid acquisition layer material to form individual absorbent article body facing liner/fluid acquisition layer combinations, each combination having a front waist region and a crotch region, wherein a first portion of the combinations has the target zone closer to the front waist region than the target zone of a second portion of the combinations, the first portion of the combinations being for use in absorbent articles for male end users and the second portion of the combinations being for use in abosrbent articles for female end users.

2. The method of claim 1, wherein the first portion of the body facing liner/fluid acquisition layer combinations has the target zone in the front waist region, and the second portion of the body facing liner/fluid acquisition layer combinations has the target zone in the crotch region.

3. The method of claim 1, wherein the target zone embossing pattern and the channel zone embossing pattern each have a bond pattern, wherein each bond pattern has a bond density, and wherein the bond density of the target zone embossing bond pattern is less than the bond density of the channel zone embossing bond pattern.

4. The method of claim 3, wherein the bond density of the target zone embossing bond pattern for an absorbent article for a male end user is different from the bond density of the target zone embossing bond pattern for an absorbent article for a female end user.

5. The method of claim 1, wherein the channel zone embossing pattern includes a generally linear figure and the target zone embossing pattern includes a figure selected from elliptical, circular, and ovate figures.

6. The method of claim 1, wherein the target zone embossing pattern includes a generally closed figure, and wherein the channel zone embossing pattern includes a generally open figure.

7. The method of claim 1, wherein the target zone embossing pattern and the channel zone embossing pattern each have a bond pattern and wherein each bond pattern has a bond density, and wherein the bond density of each bond pattern varies along a longitudinal direction of the web of bonded body facing liner material and fluid acquisition layer material.

8. The method of claim 1, wherein the target zone embossing pattern and the channel zone embossing pattern each have a bond pattern and wherein each bond pattern is registered with respect to a longitudinal axis, a transverse axis, or to both axes.

9. The method of claim 1, wherein the fluid acquisition layer material is pigmented.

10. The method of claim 1, wherein the embossing roller is phased to produce a web of bonded body facing liner material and fluid acquisition layer material having phased alternating target zone and channel zone embossing patterns with the different locations of the target zones embossing pattern in the first portion of the combinations and the second portion of the combinations is due to the phasing of the embossing roller.

11. The method of claim 1, wherein separating the web of bonded body facing liner material and fluid acquisition layer material to form individual absorbent article body facing liner/fluid acquisition layer combinations comprises adjusting the separation of the web of bonded body facing liner material and fluid acquisition layer material with respect to the alignment of the target zone and channel zone embossing patterns such that the first portion of the combinations has the target zone closer to the front waist region than the target zone of a second portion of the combinations.

\* \* \* \* \*